United States Patent [19]
Yamamoto et al.

[11] Patent Number: 5,527,516
[45] Date of Patent: Jun. 18, 1996

[54] SPRAY TYPE RETORT STERILIZER

[75] Inventors: Tutomu Yamamoto, Nara; Takashi Aomori, Nishinomiya, both of Japan

[73] Assignee: Hisaka Works Limited, Osaka, Japan

[21] Appl. No.: 232,587

[22] Filed: Apr. 25, 1994

Related U.S. Application Data

[63] Continuation of Ser. No. 938,255, Oct. 13, 1992, abandoned.
[51] Int. Cl.[6] .................... A61L 2/20; F22B 3/00
[52] U.S. Cl. ............... 422/292; 422/26; 422/298; 422/299; 159/4.08
[58] Field of Search .................. 422/26, 291, 305, 422/292, 298–299; 159/4.08

[56] References Cited

U.S. PATENT DOCUMENTS

| | | | |
|---|---|---|---|
| 2,179,256 | 11/1939 | Gill | 422/297 |
| 3,853,622 | 12/1974 | Rutten | 422/26 |
| 3,971,629 | 7/1976 | Biux et al. | 422/307 |
| 4,203,947 | 5/1980 | Young et al. | 422/26 |
| 4,242,852 | 1/1981 | Orliagust et al. | 422/297 |
| 4,395,383 | 7/1983 | Kackos | 422/26 |
| 4,489,741 | 12/1984 | Ogasawara | 134/179 |
| 5,068,087 | 11/1991 | Childers | 422/26 |

FOREIGN PATENT DOCUMENTS

| | | |
|---|---|---|
| 59-66865 | 4/1984 | Japan. |
| 61-62464 | 3/1986 | Japan. |
| 62-204753 | 9/1987 | Japan. |

*Primary Examiner*—Lyle A. Alexander
*Attorney, Agent, or Firm*—Nikaido Marmelstein Murray & Oram

[57] ABSTRACT

This invention relates to a spray type retort sterilizer which preforms various types of high-pressure sterilization. Sterilization is achieved through the use of non-atomized hot water droplets. The sterilized comprises a retort that is capable of receiving multiple trays of materials, a pressurized air intake system for introducing pressurized air into the retort, an exhaust system and multiple spray units capable of spraying liquid such that at least one spray unit is disposed adjacent to each tray of material. The invention is further defined to include a heat exchanger and a pump for removing the liquid from the retort, passing it through the heat exchanger and delivering the liquid to the spray units. The invention is further defined to include spray units that are rotatable.

3 Claims, 3 Drawing Sheets

SPRAY TYPE RETORT STERILIZER

This application is a continuation of application Ser. No. 07/938,255 filed Oct. 13, 1992 now abandoned.

BACKGROUND OF THE INVENTION

This invention relates to a spray type retort sterilizer, and more particularly a spray type retort sterilizer which performs various kinds of high-pressure sterilization of gas foods containing a lot of gas, transfusion soft pack for medicine, etc. Conventionally, various kinds of device which performs pressurized heat sterilization by using either a steam type or a hot-water type retort have been put into practice as retort sterilizer. Such devices are described in the Japanese Bulletins of Publicized Patent No. 58-57146 and No. 58-57147, for example.

In the steam type retort sterilizer, the object material to be sterilized is placed in the retort by loading the material on trays and stacking these trays. The steam outlet is designed in most cases in such a way that the steam may be discharged from the bottom of the retort toward the top. As a result, it was often the case that the object material placed on the trays at the lower part is heated at a proper temperature while the object material placed on the trays at the top part remains in the state of uneven sterilization due to a drop of temperature of the steam as it rises through the retort.

Moreover, a hot-water type retort presented a problem in that the object material stored in the trays gets unstable under the influence of the buoyancy of the hot water, requiring a complicated construction having a presser lid for the trays. The influence of the buoyancy was particularly large in the case of gas foods, while a problem with transfusion soft pack for medicine, etc. is that the very act of submerging the material in hot water is undesirable.

This inventor proposed, in the Japanese Utility Model Gazettes No. 63-16519, No. 64-19436, No. 64-19437, No. 64-19438 and No. 64-20849, a retort sterilizer which, though of steam type, can solve the above problems and enable even sterilization of the object material in the trays with fine mist sprayed from spray nozzles provided on header pipes which are installed vertically or horizontally at positions close to the tray of each stage.

By the way, in the retort sterilizer already proposed by this inventor, etc., hot water is sprayed on the object material in hot water drops of a particle size of 0.2–0.6 mm or so (in the shape of sesame particle). In that case, hot water drops of a particle size of 100° C. hot water sprayed from the nozzles instantly turn into steam by boiling and cannot be sprayed on the object material in the desired state of hot water drops if the internal pressure of the sealed retort is equal to the atmospheric pressure, for example. If you increase the size of the hot water drops, for example, to prevent such boiling phenomenon, those hot water drops cannot be sprayed to distant points. On the contrary, if you increase the spraying force to make the hot water drops go further, it leads to either breaking of the plastic pack containing the object material i.e. the material to be sterilized or deformation of the pack. Namely, the above-mentioned problem is produced as a result of softening of the plastic pack itself with the heat inside the retort.

This invention has been proposed, therefore, in view of the above problem and its object is to provide a retort sterilizer which does not produce any atomization by boiling in the retort even if the particle size of the hot water drops is 0.2–0.6 mm and the hot water temperature is 90°–130° C.

BRIEF SUMMARY OF THE INVENTION

The technical means to achieve the said object consists, of a retort sterilizer provided with a retort of sealed construction in which trays loaded with the object material to be treated are stacked in a plural number of stages, spray units which emit hot water or cooling water on the object material on the tray in each stage inside the retort and a circulation route through which to blow the water accumulated at the bottom of the retort in the form of mist from the spray units again under pressure through a pump and a heat exchanger. The present invention also includes an internal pressure adjusting system composed of a pressurized air intake system which introduces pressurized air into the retort and an exhaust system which evacuates gas from inside the retort.

In a spray type retort sterilizer according to this invention, the internal pressure of the sealed retort is set at a pressure at which the desired hot water drops are not instantly atomized by boiling with mutual operations of the pressurized air intake system which introduces pressurized air into the retort and the exhaust system which evacuates gas from inside the retort. Therefore, even with hot water of a temperature of 90°–130° C., it is possible to blow hot water drops of a particle size of 0.2–0.6 mm uniformly against the object material and equalize the temperature in the entire area of spraying to ensure a treatment of high efficiency.

With a spray type retort sterilizer according to this invention, provided with a pressurized air intake system which introduces pressurized air into the retort and a exhaust system which evacuates gas from inside the retort, the internal pressure of the sealed retort can be set at a pressure at which the desired hot water drops are not instantly atomized by boiling with mutual operations of the pressurized air intake system which introduces pressurized air into the retort and the exhaust system which evacuates gas from inside the retort. As a result, it becomes easy to provide a retort sterilizer of high practical value which can blow desired hot water drops exactly and uniformly against the object material and equalize the temperature in the entire area of spraying to ensure a treatment of high efficiency.

DETAILED DESCRIPTION OF THE PREFERRED EMBODIMENT

Figure 1:
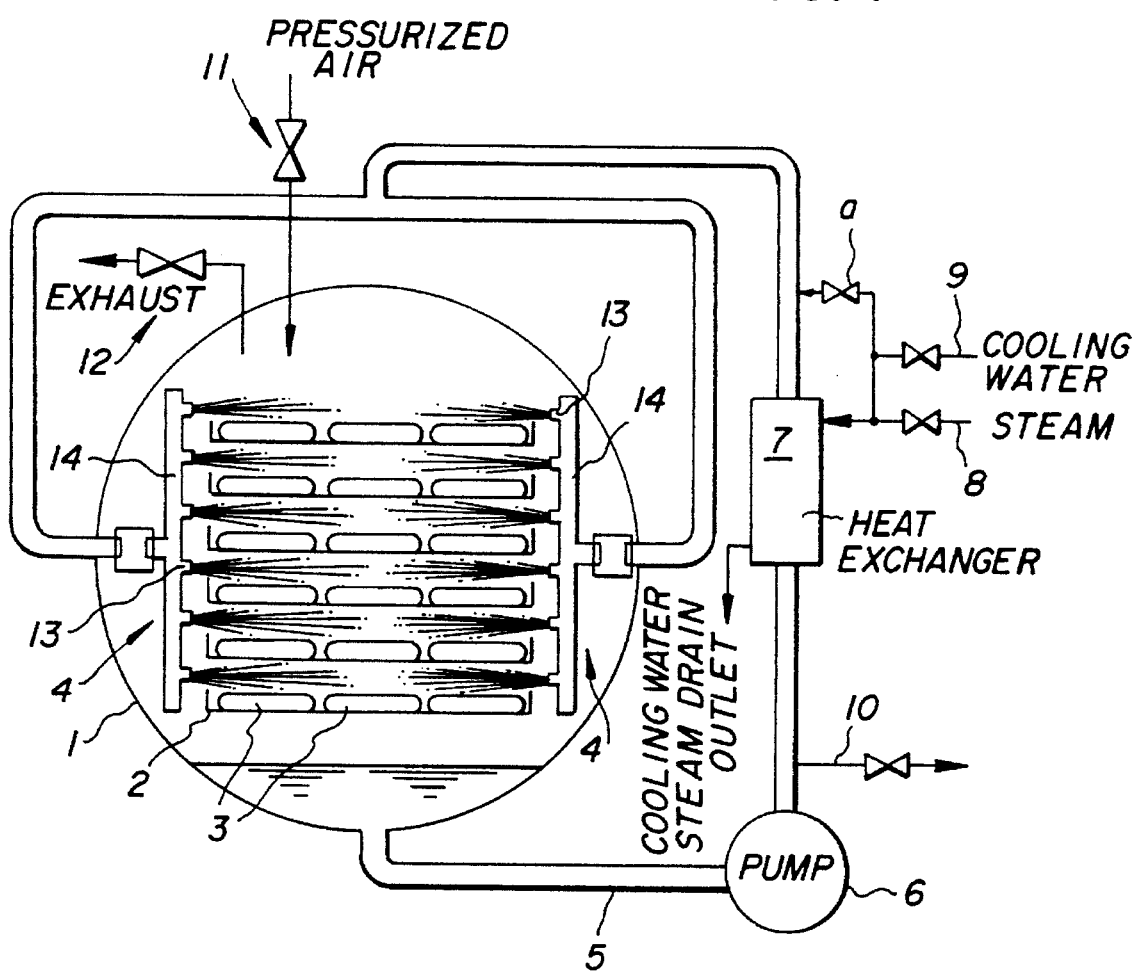
FIG. 1 is an approximate construction drawing showing an example of the spray type retort sterilizer according to this invention.
Figure 2:
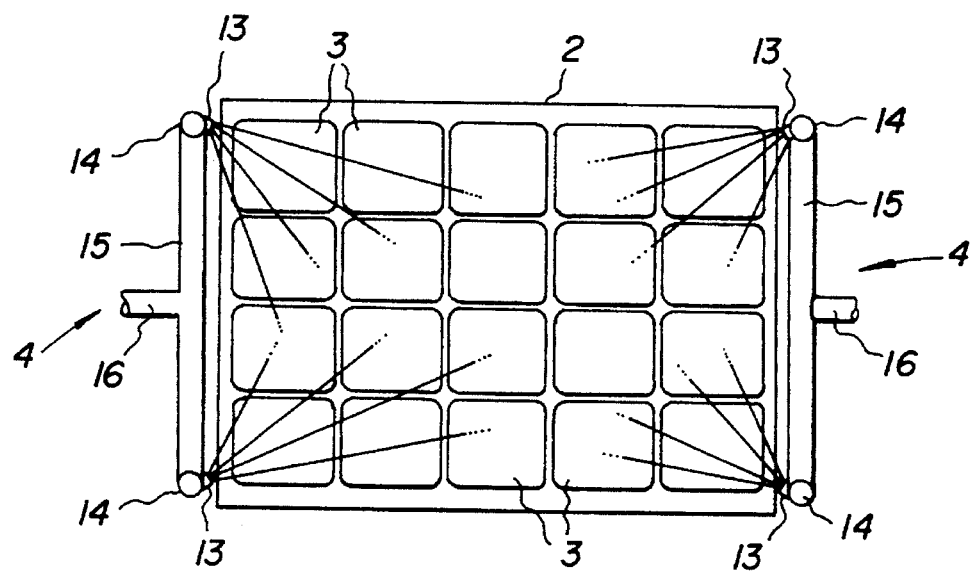
FIG. 2 is a plan view showing the tray, the object material and the sprays of FIG. 1.
Figure 3:
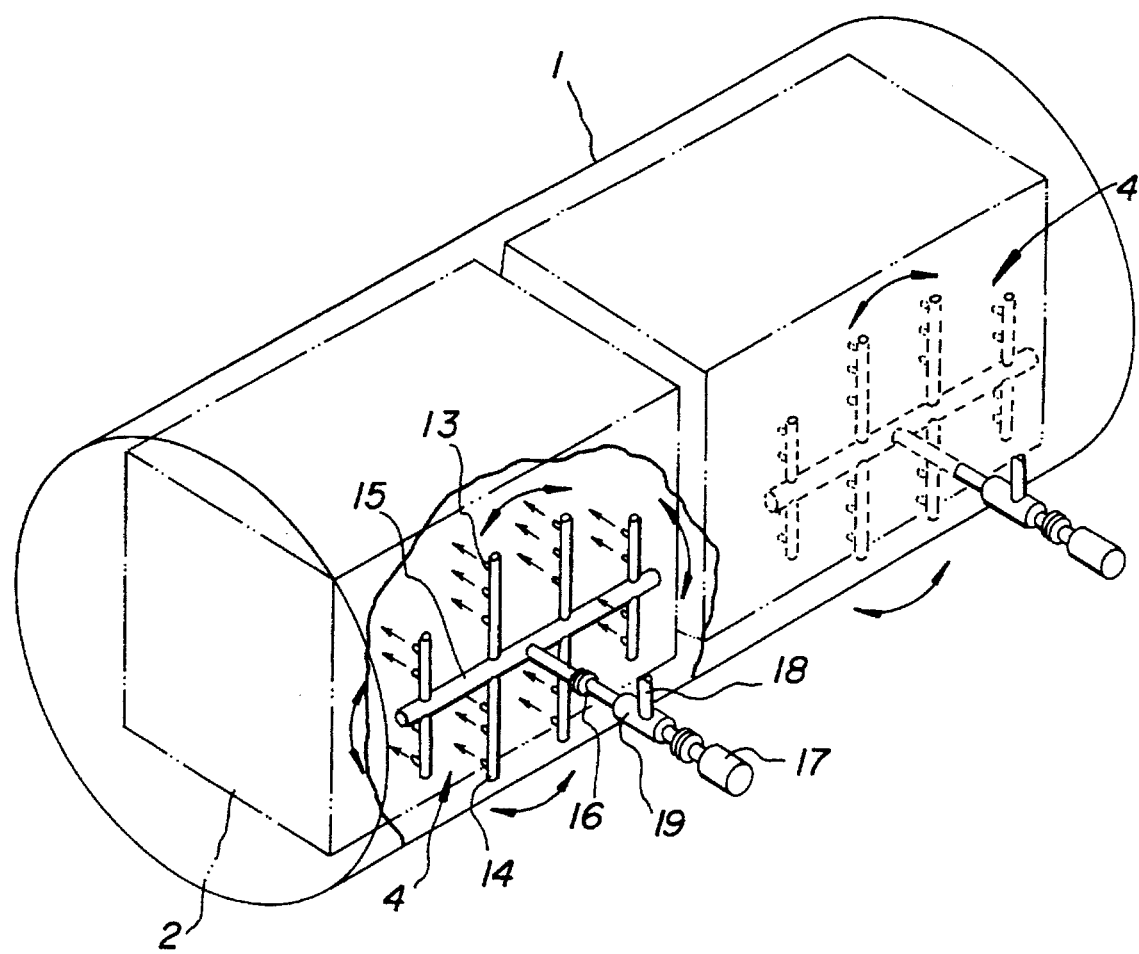
FIG. 3 is a partial perspective view showing the tank and the spray unit of FIG. 1.

An example of the spray type retort sterilizer according to this invention is shown in FIG. 1 to FIG. 4. FIG. 1 is an approximate construction drawing of the spray type retort sterilizer according to this invention, FIG. 2 is a plan view showing the tray, the object material and the sprays and FIG. 3 is a partial perspective view showing the tank and the spray unit.

In the spray type retort sterilizer indicated in FIG. 1, (1) is the tank constituting the retort of the retort sterilizer and is sealed during the treatment work. (2) are the plural numbers of stacked trays which are disposed inside the tank (1) so as to define stages. (3) is the object material arranged on the tray (2) consisting of gas foods, transfusion soft pack for medicine, etc. sealed in plastic packs containing a large quantity of gas to be submitted to high-pressure sterilization. (4) are the spray units disposed on both sides in each stage of the plural number of trays (2) inside the tank (1), intended to atomize and spray hot water or cooling water in the shape of sesame particles of a particle size of 0.2–0.6 mm or so, in the horizontal direction in the shape of a fan for example, on the object material for treatment (3) in such a way that the spray may reach the entire surface of the tray (2) in each stage. (5) is the circulation route mounted on the tank (1) to blow the water accumulated at the bottom of the tank (1) as hot water or cooling water in the form of sesame particles from the spray unit again under pressure through the pump (6) and the heat exchanger (7). In the heating process, the circulating water flowing in the circulation route (5) is gradually heated with the steam (8) indirectly and this hot water is sprayed from the spray unit (4) in the tank (1) toward the object material for treatment (3) on the tray. When this heating process is over, cooling water (9) is supplied instead of the steam (8) as heat source of the heat exchanger (7) provided outside the tank (1) to gradually cool the hot water in the circulation route (5), which was used for spraying, indirectly with the heat exchanger (7), and this water is eventually sprayed on the object material for treatment (3) on the tray (2) from the spray unit (4) in the tank (1) at a temperature 3°–5° C. higher than that of the cooling water. Moreover, the cooling water (9) is directly supplied to the spray unit (4) through the bypass valve (a) as required when the temperature of the circulating water dropped to some extent to a temperature area in which there is no fear of deformation of the formed container of the object material for treatment (3). [a temperature difference of 20° C. or so for example, although this temperature varies depending on the product to be treated]. When suppling the cooling water (9) directly from the circulation route (5) to the spray unit (4) through the bypass valve (a), the water inside the tank (1) is evacuated through the drain valve (10) on the discharge side of the pump (6) to prevent the liquid level in the tank (1) from going up. (11) and (12) are a pressurized air intake system and an exhaust system described later characterizing this invention mounted on the tank (1). The pressurized air intake system (11) introduces pressurized air into the tank (1) while the exhaust system (12) exhausts gas from inside the tank (1).

The spray unit (4) consists of a plural number of header pipes (14) having a large number of spray nozzles and disposed in upright position as shown in FIG. 2 and FIG. 3, the pitch of spray nozzles (13) being set equal to the pitch of piling of the trays (2). Of the plural number of header pipes (14), the header pipes (14) at both ends are formed a little shorter than others. In the same drawings, (15) are connecting pipes for introduction and connect the plural number of header pipes (14) at the center collectively and horizontally. (16) is an introducing pipe which is connected to the center of the connecting pipes for introduction (15) to lead to outside of the tank (1). (17) is a drive source such as torque actuator, etc., for example, provided outside the tank (1) and used to make the header pipes (14) rotationally oscillate in the vertical face with the introducing pipe (16) as central axis. (18) is the inlet of hot water or cooling water and communicates to the header pipes (14) through the introducing pipe (16) and the connecting pipes for introduction (15) by means of a communicating section (19) consisting of a rotary joint, etc., for example.

The spray unit (4) is not necessarily limited to the said construction but may be constructed in such a way as provide a plural number of header pipes horizontally to make them rotationally oscillate or provide a plural number of header pipes vertically to make them move up and down in the vertical direction.

Next, a concrete composition of a retort sterilizer according to this invention will be described based on FIG. 4. However, the details of the tank (1), the trays (2), the object material for treatment (3) and the spray unit (4) will be omitted to avoid duplication of explanation since they have already been described above.

The heat exchanger (7) is a plate type heat exchanger having a heat receiving section (7a) and a heat discharging section (7b), the heat receiving section (7a) being connected to the bottom part of the tank (1) and the spray unit (4) so that the water at the bottom inside the tank (1) may be blown from the spray nozzles of the spray unit (4) in the form of water drops of desired particle size by the pump (6) through the heat receiving section (7a). The heat discharging section (7b) of the heat exchanger (7) is connected at one end in a switchable way with the steam source (20) and the cooling water inlet (21) through the stop valve for steam (22) of the heat exchanger and the cooling water inlet valve (23), and is connected at the other end with the cooling water outlet (25). In the drawing, (26) is a gate valve, (27) is an air vent valve for pump, (28) is a relief valve for heat exchanger, (29) is a cone strainer, (30) is a gate valve and (31) is a bypass valve for heat exchanger, all constituting the heat receiving system. (32) is a strainer for steam inlet, (33) is a stop valve for steam inlet, (34) is a steam inlet valve, (35) is a temperature regulating steam valve, (36) is a cooling water switching valve and (37) is a safety valve for heat exchanger, all constituting the heat discharging system. (38) is a drain & waste water outlet branching from the piping between the tank (1) and the pump (6), and is connected with the piping between the heat discharging section (7b) and the cooling water outlet (25) through a steam trap valve (39) and a steam trap (40). (41) is a waste water valve. (42) is a water source connected to the vicinity of the suction port of the pump (6) through a feed water check valve (43), a feed water stop valve (44) and a feed water valve (45) and supplying cooling water to the pump (6) through a cooling water stop valve for pump (46).

Figure 4B:
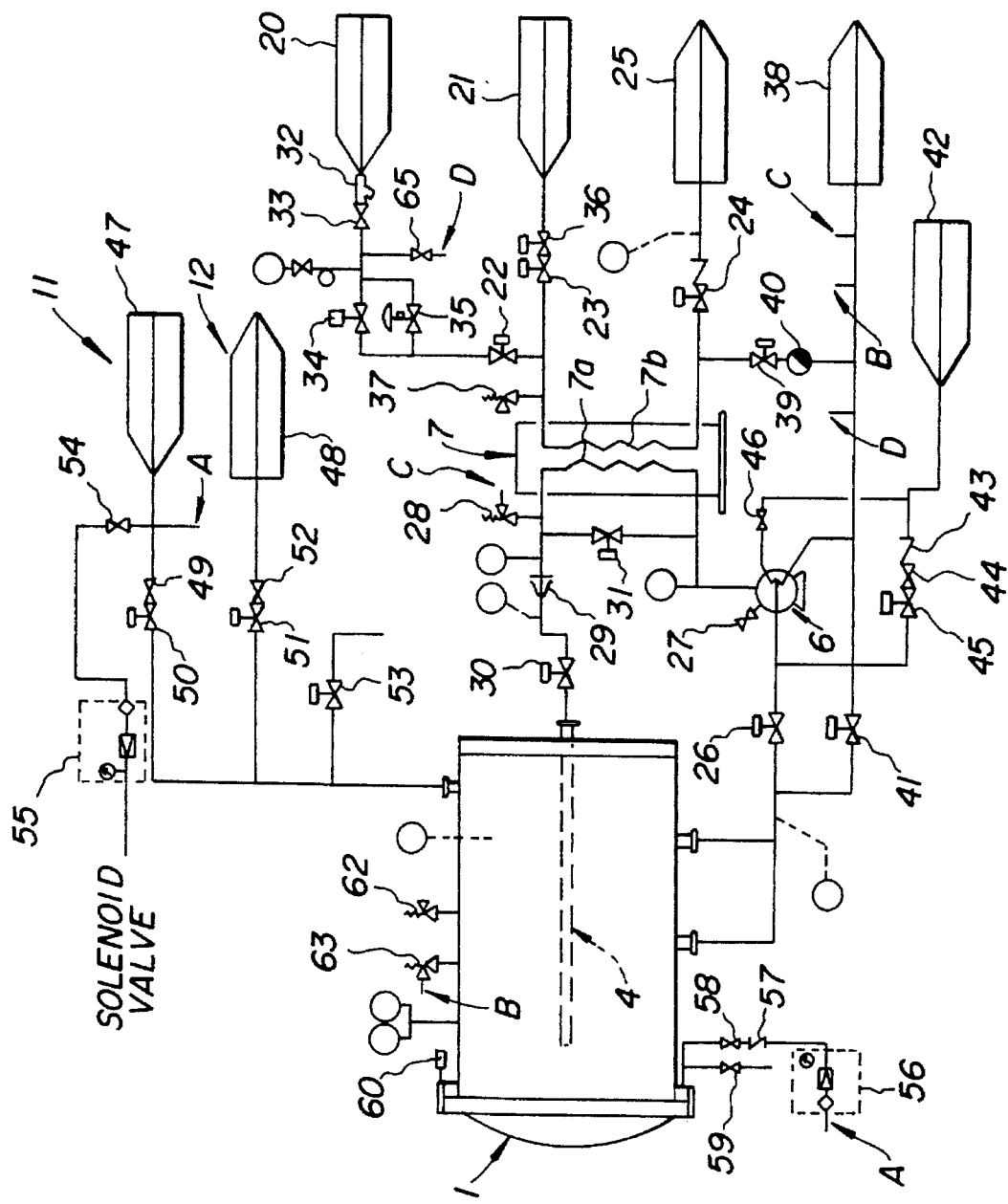
FIG. 4 is a flow sheet showing a concrete construction of a spray type retort sterilizer of FIG. 1.
Figure 4A:
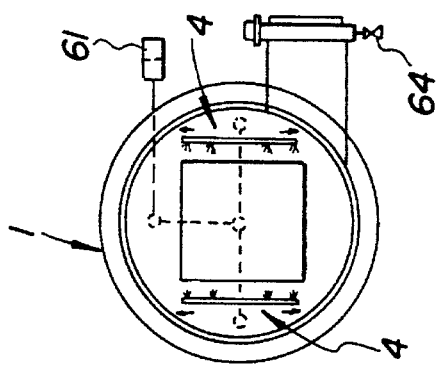

In FIG. 4, (11), (12) are a pressurizd air intake system and an exhaust system constituting the main part of this invention and form an internal pressure regulating system of the tank (1) which regulates the internal pressure of the tank (1) by introducing pressurized air into the tank (1) with the pressurized air intake system (11) to prevent the water drops gushing from the spray nozzles (13) inside the tank (1) from instantly evaporating and discharges gas from inside the tank (1) with the exhaust system (12). (47) is a pressurized air source and (48) is an exhaust port and the pressurized air is supplied to the top part of the tank (1) through a stop valve for pressurized air (49) and a pressurizing valve (50). Branching from the piping between the tank (1) and the pressurizing valve (50) are a pipe line connected to the exhaust port (48) through an air vent valve (51) and a stop valve for exhaust air (52) and a pipe line opening in the atmosphere through an air intake valve (53). The said pressurized air is supplied not only to a solenoid valve through a stop valve for operating air (54) and a pressure reducing valve with filter (55) but also to the lid driving section through a pressure reducing valve with filter (56), a check valve for air (57) and a packing clamping valve (58). (59) is a packing opening valve, (60) is an air cylinder for locking the lid, (61) is a nozzle driving air cylinder, (62) is a vacuum breaker, (63) is a relief valve for tank and (64), (65) are drain cocks. The end parts (A), (B), (C), (D) of the pipe lines in the drawing are not illustrated but are connected with those of the same symbol respectively.

In a retort sterilizer having a construction as described above, the header pipes (14) of the spray unit (4) having a large number of spray nozzles connected integrally through the communicating section (19), the introducing pipe (16) and the connecting pipes for introduction (15) rotationally oscillate in the vertical face with the operation of the drive source (17) and, while repeating this rotational oscillation, eject hot water or cooling water taken from the inlet (18) from the spray nozzles (13) via the connecting pipes for introduction (15) and the introducing pipe (16). The hot water or cooling water from the spray nozzles (13) is uniformly distributed around the tray (2) with the rotational oscillation of the header pipes (14) in a way to be uniformly sprayed on the object material for treatment (3) on the tray (2), thus ensuring uniform sterilization of the object material for treatment (3) regardless of the stacking condition of the trays (2).

If, at this time, the internal pressure of the sealed tank (1) is equal to the atmospheric pressure, hot water drops of a particle size of 100° C. hot water ejected from the spray nozzles (13) instantly turn into steam by boiling and cannot be sprayed on the object material for treatment (3) in the desired state of hot water drops. For that reason, the internal pressure of the tank (1) is adjusted in correspondence to the sprayed hot water temperature with an internal pressure regulating system of the tank (1) composed of the pressurized air intake system (11) and the exhaust system (12). Namely, the internal pressure of the tank (1) can be set at a pressure at which the desired hot water drops are not instantly atomized by boiling with mutual operations of the pressurized air intake system (11) which introduces pressurized air into the tank (1) and the exhaust system (12) which evacuates gas from inside the tank (1). Therefore, even with hot water of a temperature of 90°~130° C., it is possible to blow hot water drops of a particle size of 0.2~0.6 mm uniformly against the object material and equalize the temperature in the entire area of spraying of ensure a treatment of high efficiency without any need of increasing the size of the hot water drops.

What is claimed is:

1. A retort sterilizer comprising:

a retort capable of receiving multiple trays of material to be treated so as to define stages;

a pressurized air intake means for pressurizing the retort to a pressure greater than normal pressure;

an exhaust system for evacuating gas from the retort; and multiple spray units within said retort capable of spraying liquid in particle sizes of 0.2–0.6 mm, wherein said spray units are disposed such that at least one spray unit is disposed adjacent to each of said stages.

2. A retort sterilizer as in claim 1, further comprising:

a heat exchanger; and a pump means for removing said liquid from the retort, passing it through said heat exchanger, and delivering said liquid to said spray units.

3. A retort sterilizer as in claim 1, wherein the multiple spray units are rotatable.

\* \* \* \* \*

UNITED STATES PATENT AND TRADEMARK OFFICE
CERTIFICATE OF CORRECTION

PATENT NO. : 5,527,516
DATED      : June 18, 1996
INVENTOR(S) : Yamamoto et al.

It is certified that error appears in the above-indentified patent and that said Letters Patent is hereby corrected as shown below:

On title page, item [63], should read
--Continuation of Ser. No. 938,255, filed Oct. 13, 1992, abandoned, filed as PCT/JP91/00331, filed March 11, 1991--.

Signed and Sealed this

Third Day of December, 1996

Attest:

BRUCE LEHMAN

*Attesting Officer*     Commissioner of Patents and Trademarks